United States Patent
Feeley et al.

(10) Patent No.: US 8,123,728 B2
(45) Date of Patent: Feb. 28, 2012

(54) ANTIMICROBIAL AGENT DELIVERY SYSTEM

(75) Inventors: Kristin Feeley, Hingham, MA (US); Ray Lareau, Westford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/767,620

(22) Filed: Apr. 26, 2010

(65) Prior Publication Data

US 2010/0274201 A1    Oct. 28, 2010

Related U.S. Application Data

(62) Division of application No. 10/786,021, filed on Feb. 26, 2004, now abandoned.

(51) Int. Cl.
*A61M 5/32* (2006.01)
(52) U.S. Cl. .................................................. 604/265
(58) Field of Classification Search ............... 604/161, 604/171, 57, 59, 164.08, 93.01, 164.01, 164.06, 604/263, 264
See application file for complete search history.

(56) References Cited

U.S. PATENT DOCUMENTS

| | | | |
|---|---|---|---|
| 3,595,230 A | 7/1971 | Suyeoka et al. | |
| 5,357,978 A | 10/1994 | Turk et al. | |
| 5,419,766 A | 5/1995 | Chang et al. | |
| 5,509,912 A * | 4/1996 | Vaillancourt et al. | 604/537 |
| 6,726,658 B2 | 4/2004 | Hochman | |
| 6,838,050 B1 | 1/2005 | Green et al. | |
| 2002/0055733 A1* | 5/2002 | Wilson | 604/528 |
| 2003/0175323 A1 | 9/2003 | Utterberg et al. | |
| 2003/0212373 A1 | 11/2003 | Hall et al. | |
| 2003/0236552 A1 | 12/2003 | Roby | |
| 2004/0230162 A1* | 11/2004 | Tan | 604/171 |

FOREIGN PATENT DOCUMENTS

| | | |
|---|---|---|
| WO | 00/09185 | 2/2000 |
| WO | 00/67647 | 11/2000 |
| WO | 01/36029 | 5/2001 |
| WO | 01/89605 | 11/2001 |

* cited by examiner

*Primary Examiner* — Christopher D Koharski
(74) *Attorney, Agent, or Firm* — Mayer & Williams PC; David B. Bonham; Keum J. Park

(57) ABSTRACT

An antimicrobial agent delivery system and method are provided for an antimicrobial agent-bearing intervention device. A delivery tube contains the intervention device, where the delivery tube facilitates handling of the intervention device. In one example, the intervention device is a rod, and a hub is coupled to the rod. Longitudinal movement of the hub ejects the rod from the delivery tube.

20 Claims, 4 Drawing Sheets

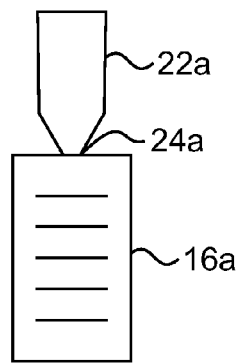
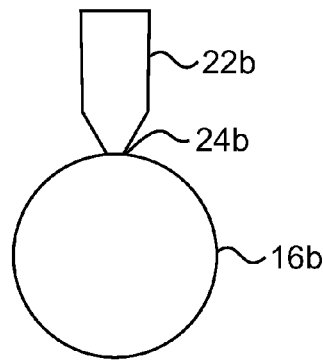
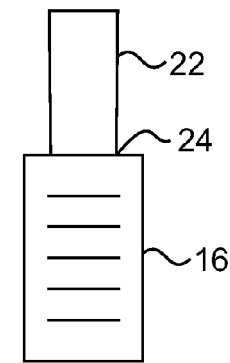
FIG. 5A     FIG. 5B     FIG. 5C
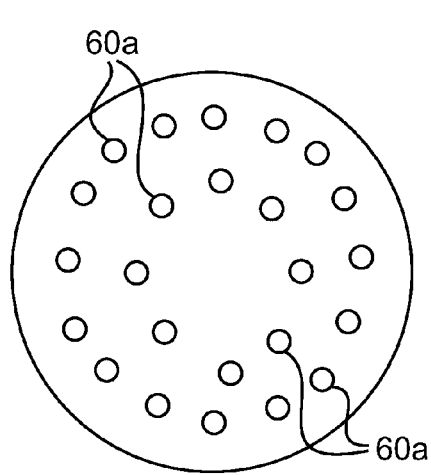
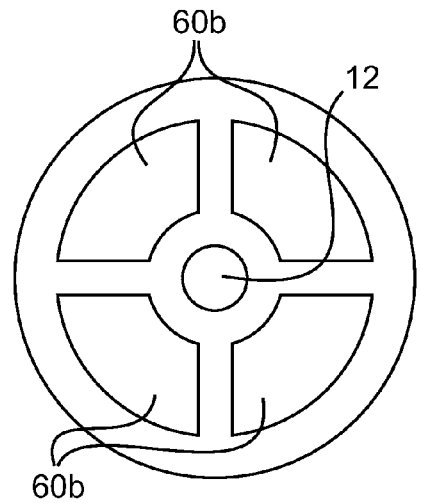
FIG. 6A     FIG. 6B

ANTIMICROBIAL AGENT DELIVERY SYSTEM

RELATED APPLICATIONS

This application is a divisional application of co-pending U.S. patent application Ser. No. 10/786,021, filed Feb. 26, 2004, which is incorporated by reference in its entirety herein.

FIELD OF THE INVENTION

Embodiments of the present invention are directed to an improved system and method for delivering antimicrobial agents into catheters.

BACKGROUND

Catheters have become widely used in modern medicine to provide one or more lumens into a patient's body through which a wide variety of procedures may be performed or fluids may be introduced or removed from the patient. Examples include catheters lumens through which minimally-invasive surgical procedures, such as angioplasty balloon deployment or tissue resection, may be performed, catheters for introducing therapeutic substances at desired sites within the patient, catheters for the removal and/or replacement of fluids, such has blood removal and replacement during hemodialysis, and catheters associated with activation of mechanisms for medical devices, such as activation of control cables or application of pneumatic pressure to inflate balloons or expand stents at target locations within the patient.

Inherent with the use of medical devices placed within a patient is the risk of infection from the medical device. While great strides have been made in the last century in preventing infection during surgical procedures, this risk has not been entirely eliminated. For example, it has been estimated that central venous catheters account for more than 90 percent of all nosocomial catheter-related blood stream infections.

In the case of central venous catheters, characteristically, at an infected site a large number of microorganisms are adherent on the catheter, where there is an interaction between the pathogen and the catheter microsurface. Once so infected, the microorganisms adhere to the catheter and rapidly become encased in a polysaccharide matrix or biofilm which protects the microorganisms from the natural defenses of the host. While there have been recent developments of central venous catheters to attempt to reduce the incidence of nosocomial catheter-based infections, such as the use of catheters with liquid chlorohexidine and silver sulfadiazine, or with a combination of minocycline and rifampin, such infections have yet to be eliminated.

The use of antimicrobial agent-bearing intervention devices has been proposed for the management of nosocomial blood stream infections. Antimicrobial agents such as povidone-iodine, chlorhexidine, polymicrobial gel, isopropyl alcohol and hydrogen peroxide have long been used in medical practice as disinfectants, with iodine having been discovered to be one of the most effective antiseptics in the 1870s. Recently, iodine-bearing formulations have been developed that may be applied to, or incorporated into, medical devices to provide controlled in-situ release of iodine as an antimicrobial agent. One potential application of such formulations is an iodine-bearing polymeric rod that can be inserted into a catheter, where the rod delivers iodine to the catheter in order to manage catheter-based nosocomial bloodstream infections. In this example, an iodine-bearing polymeric intervention device is placed within an indwelling catheter. As a result, elemental iodine may be released to diffuse to the catheter wall, and if the catheter wall material is semi-permeable, to diffuse through the catheter wall to the exterior surface of the catheter. Thus, the iodine may be made available to eliminate micro-organisms on both the inner and outer microsurfaces of the catheter.

Notwithstanding the advantages in catheter-based nosocomial blood stream infection management offered by the use of an iodine-bearing polymeric intervention device, installation or delivery of the device into the catheter presents a number of challenges. For example, during insertion into the catheter, it is highly desirable for the intervention device to remain sterile and, therefore, out of direct contact with equipment, hands, and any other non-sterile surfaces. In addition, due to the relatively low column strength of rod implementations of the intervention devices, control over the rod can be less than desired. There is therefore a need for a delivery system that provides sterility by reducing direct handling of antimicrobial agent-bearing intervention devices. There is also a need for a delivery system that enhances control over the insertion of the intervention device during insertion into the catheter lumen.

SUMMARY OF THE INVENTION

In accordance with certain embodiments of the invention, systems and methods of delivering antimicrobial agent-bearing intervention devices are provided for reduced handling and improved control of the intervention device.

In one embodiment, an antimicrobial agent delivery system includes an antimicrobial agent-bearing intervention device and a delivery tube containing the intervention device. The delivery tube facilitates manipulation of the intervention device.

In another embodiment of the invention, an antimicrobial agent delivery system includes an antimicrobial agent-bearing rod, a delivery tube, and a hub. The delivery tube contains the rod, and the delivery tube facilitates manipulation of the rod. The hub is coupled to the rod, and movement of the hub ejects the rod from the delivery tube. The delivery tube may have a longitudinal partition and a hub opening, where the hub opening provides external access to the hub and the longitudinal partition guides the hub longitudinally. The hub is optionally disposed within the delivery tube. An extension arm may be connected to the hub and may extend through the hub opening. If desired, the extension arm may be connected to the hub at a tapered connection point, where the tapered connection point enables removal of the extension arm from the hub after ejection of the rod from the delivery tube.

In yet another embodiment, a method of fabricating an antimicrobial agent delivery system provides for coupling a hub to an antimicrobial agent-bearing rod. A longitudinal partition and a hub opening are formed in a delivery tube. The method further provides for disposing the rod within the delivery tube, where the hub opening provides external access to the catheter hub.

BRIEF DESCRIPTION OF THE DRAWINGS

The foregoing and further objects, features and advantages of the invention will become apparent from the following detailed description with reference to the accompanying drawings, wherein like numerals are used to represent like elements and wherein:

FIG. 5A is a side view of an example of a tapered connection point between a hub and an extension arm according to an embodiment of the invention;

FIG. 5B is an end view of an alternative example of a tapered connection point between a hub and an extension arm according to another embodiment of the invention;

FIG. 5C is a side view of a example of a non-tapered connection between a hub and an extension arm according to another embodiment of the invention;

FIG. 6A is an end view of an example of a hub having surfaces defining one or more apertures that enable fluid transfer according to an embodiment of the invention;

FIG. 6B is an end view of another example of a hub having surfaces defining one or more apertures that enable fluid transfer according to another embodiment of the invention;

DETAILED DESCRIPTION

Some possible embodiments of the invention are hereafter described. One embodiment of the present invention is illustrated in FIGS. 1A-1C.

Figure 1A:
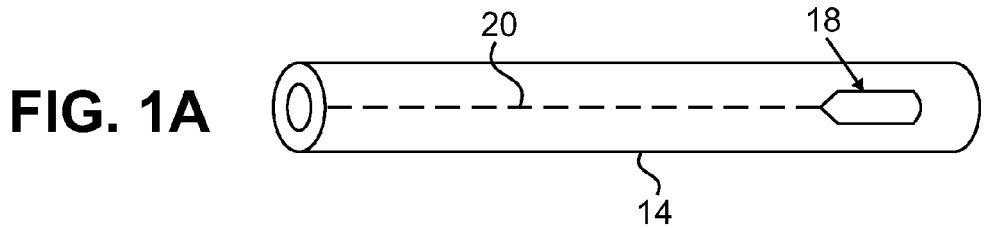
FIG. 1A is a side view of an example a delivery tube according to one embodiment of the invention.

FIG. 1A shows a delivery tube 14. The delivery tube 14 has a longitudinal partition, in this case a perforation 20, and a hub opening 18. The longitudinal partition may be perforated, as shown, pre-scored, a continuous slit, or any other configuration that enables the functioning as described below.

Figure 1B:
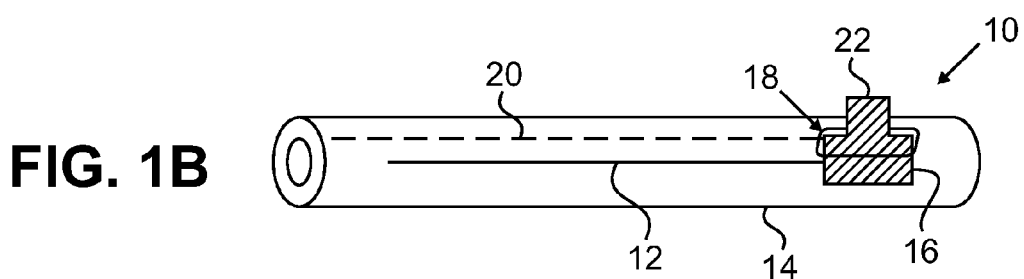
FIG. 1B is a side view of an example of an antimicrobial agent delivery system before ejection according to one embodiment of the invention.
Figure 1C:
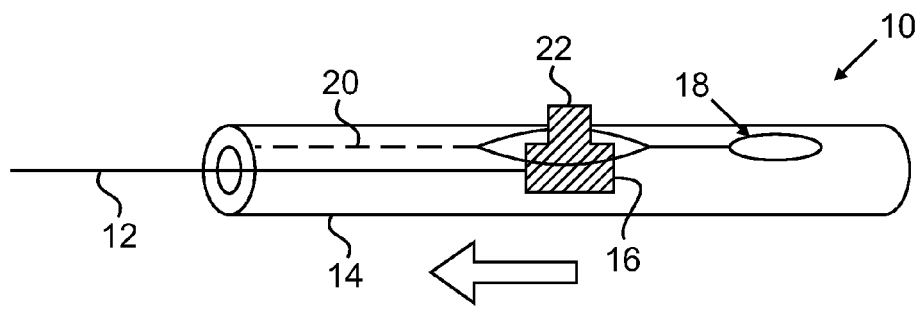
FIG. 1C is a side view of an example of an antimicrobial agent delivery system during ejection according to one embodiment of the invention.

FIGS. 1B and 1C show an antimicrobial agent delivery system 10. The antimicrobial agent delivery system 10 includes an antimicrobial agent-bearing intervention device, such as rod 12, and the delivery tube 14. The antimicrobial agent-bearing intervention device may have any suitable geometry. For example, it may be a tube or have an irregular shape, etc. Similarly, the delivery tube may have any suitable geometry. For example, it may have a cross-sectional geometry that is similar to or different from the cross-sectional geometry of the intervention device.

In the assembled configuration shown in FIG. 1A, the antimicrobial agent-bearing intervention device is a rod 12 is disposed within the delivery tube 14. The delivery tube 14 facilitates manipulation of the rod 12. That is, because the rod 12 is in the delivery tube 14, the rod 12 can be moved by simply grasping the delivery tube 14, without the need to handle the rod 12 itself.

A hub 16 is coupled to the rod 12. In this illustrated embodiment, an extension arm 22 is coupled to the hub 16. In the assembled configuration shown in FIG. 1A, the extension arm 22 extends through the hub opening 18.

The operator can eject the rod 12 from the tube 14 by longitudinally moving the hub 16 via extension arm 22. The hub opening 18 provides external access to the hub 16, and the perforation 20 guides the hub 16 longitudinally. Longitudinal movement of the hub 16 results in ejection of the rod 12 from the delivery tube 14. Thus, without touching the rod 12, the rod 12 can be removed from the delivery tube 14 for use with a catheter.

FIG. 5A shows an embodiment in which the extension arm 22a is tapered toward the point where it connects with the hub 16a, such that the extension arm 22a and the hub 16a have a tapered connection point 24a. In FIG. 5A, the width of the extension arm 22a is tapered. FIG. 5B shows an alternative embodiment in which the thickness of the extension arm 22b is tapered toward the point where it connects with the hub 16b, such that the extension arm 22b and the hub 16b have a tapered connection point 24b. The tapered connection point 24a or 24b enables removal of the extension arm from the hub after ejection of the rod from the delivery tube 14 (FIGS. 1A-1C). The tapered connection may have other suitable configurations, or other types of geometries or structures may be used, to facilitate separation of the extension arm from the hub, if desired. Of course, the extension arm need not be tapered, as shown in FIG. 5C, leaving a non-tapered connection point 24.

Figure 2:
FIG. 2 is a side view of an example of antimicrobial agent delivery system according to another embodiment of the invention.

Turning now to FIG. 2, another embodiment of an antimicrobial agent delivery system is shown. In this embodiment, a delivery system 31 includes an antimicrobial agent-bearing rod 26 and a delivery tube 32. The antimicrobial agent-bearing rod 26 has a flex point 28. A hub 30 is connected to the end of the antimicrobial agent-bearing rod and is disposed outside the delivery tube 32. It should be noted that disposing the hub 30 outside the delivery tube 32 enables the delivery tube 32 to be reduced in size considerably. It should also be noted that the illustrated delivery tube 32 has a longitudinal partition, where the partition is a continuous slit 34 rather than a perforation. In such a case, it may be advantageous to structure the material of the delivery tube to enable the slit 34 to be self-sealing. One such material would be thermoplastic polyurethane (TPU), which has a low durometer characteristic to provide a desired level of "tackiness" on the surfaces that define the slit 34. The resulting slit 34 would provide a dynamic seal that can be broken and immediately re-sealed as the rod 26 is advanced through the delivery system 31.

Figure 3:
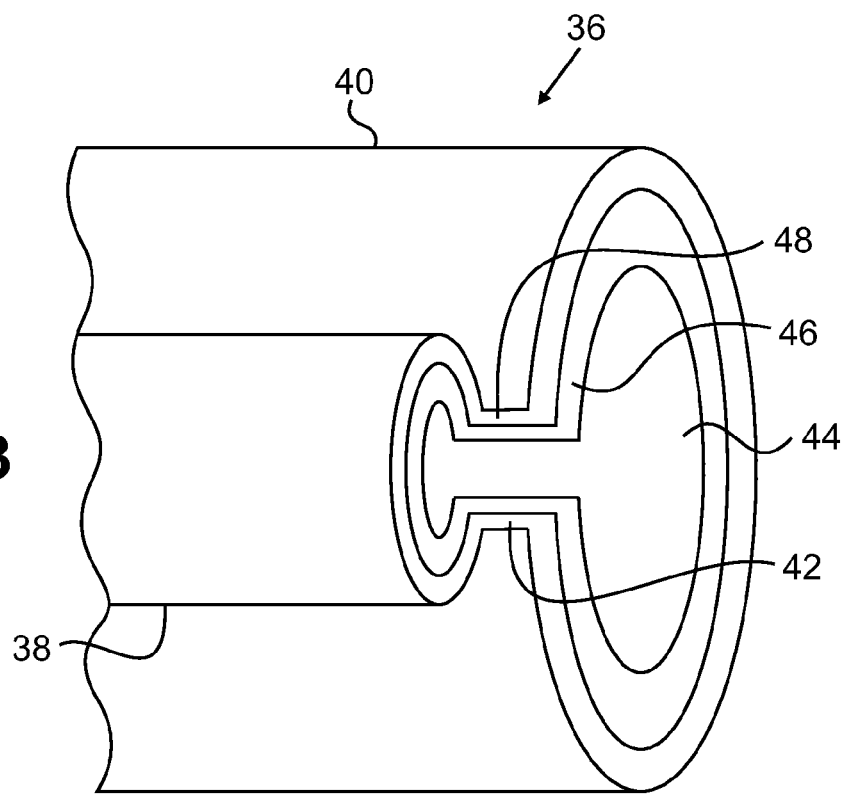
FIG. 3 is a side view of an example of an antimicrobial agent delivery system having a multiple lumen geometry according to another embodiment of the invention.

FIG. 3 shows another alternative embodiment of an antimicrobial agent delivery system in which a delivery tube 36 has a multiple lumen geometry. The multiple lumen geometry is defined by a first tube 38 and a second tube 40. An antimicrobial agent-bearing rod 42 is disposed within the first tube 38. The rod 42 may be connected to a hub 44 that is disposed within the second tube 40. Alternatively, the rod 42 may be connected to a hub disposed within the first tube 38, and the hub may be connected to an extension arm that extends into the second tube 40. The rod 42 connects to the hub 44 (or the extension arm projects) through a longitudinal partition 46 defined by surfaces in a wall 48 that connects the first tube 38 to the second tube 40. The hub and rod can be advanced through the delivery tube 36 by manipulating an extension arm (not shown) along a longitudinal partition formed in the second tube 44, by manipulating a plunger (not shown) into second tube 40 to act on the extension arm or hub, or by any other suitable actuation structure.

Turning now to FIG. 4, another embodiment of an antimicrobial agent delivery system is shown. In this embodiment, a delivery system 50 includes a plunger 52 extending out of an end of a delivery tube 54, where the plunger 52 is in contact with a hub 56. The hub 56 is attached to an antimicrobial agent-bearing rod 58. The delivery tube 54 has openings at both ends to accommodate the longitudinal movement of the plunger 52 as well as the rod 58. It should be noted that this delivery system 50 does not require a longitudinal partition.

Figure 4:
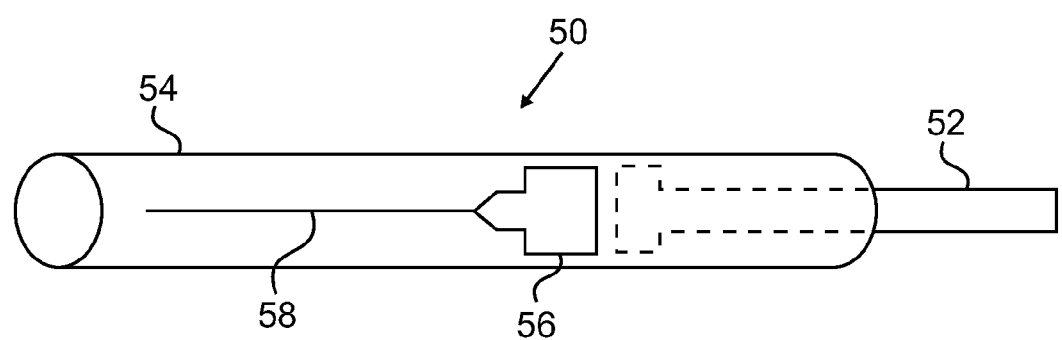
FIG. 4 is a side view of an example of an antimicrobial agent delivery system having a plunger according to another embodiment of the invention.

Turning now to FIG. 6A, an end view of a hub is shown. The illustrated hub has surfaces defining one or more apertures 60a that enable fluid transfer through the hub while the antimicrobial agent-bearing rod is installed in a catheter (not shown). FIG. 6B shows another possible configuration of apertures 60b. With the apertures, the hub enables flushing and aspiration to take place around the rod. The apertures can be readily included in hub 16 (FIGS. 1A-1C), hub 30 (FIG. 2), hub 44 (FIG. 3), and hub 56 (FIG. 4).

The outer surface of the above-described delivery tubes can include materials such as polyether block amide (PEBA), polyethylene, thermoplastic polyurethane (TPU), polyester elastomer, ionomer and thermoplastic vulcanizate to provide a relatively high surface texture. The result would be improved ergonomics and enhanced control. It should also be noted that the inner surface of the delivery tubes can include materials that are non-permeable to the particular antimicrobial agent being used. For example, in the case of iodine, the inner surface of the delivery tube may include PET.

Figure 7A:
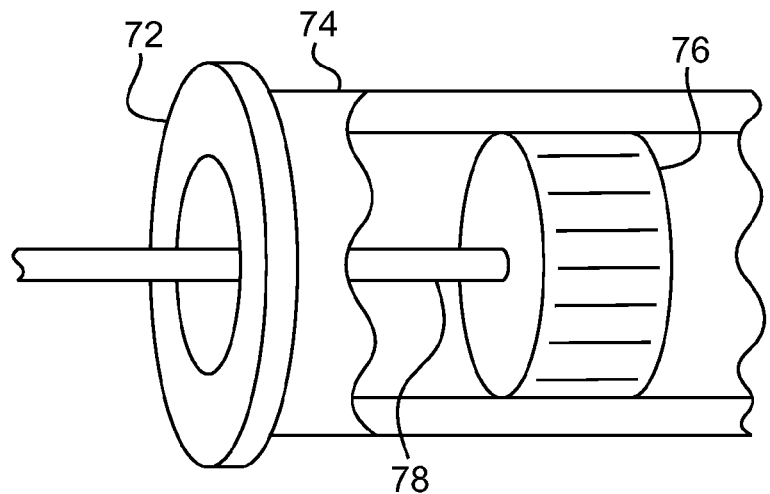
FIGS. 7A and 7B are cut-away views of an example of a valve according to an embodiment of the invention.
Figure 7B:
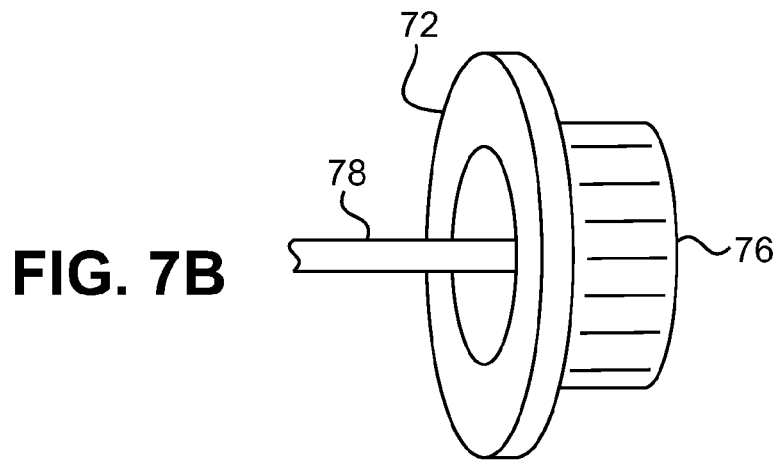

FIGS. 7A and 7B show a valve 72 that can be incorporated into an anti-microbial agent delivery system such as any of the systems discussed above. Valve 72 is coupled to an open end of a delivery tube 74, where the delivery tube 74 contains a hub 76 and rod 78. The valve 72 attaches to the hub 76 and detaches from the delivery tube 74 when ejection of the rod 78 is complete. The valve 72 attached to the hub 76 as shown in FIG. 7B enables the flow of fluid to and from a catheter (not shown) to be restricted as desired.

Figure 8:
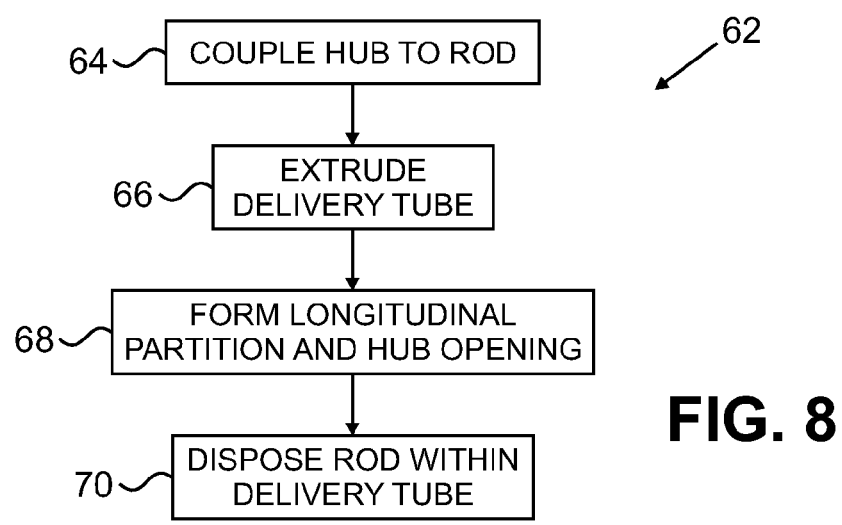
FIG. 8 is a flowchart of an example of a method of fabricating an antimicrobial agent delivery system according to one embodiment of the invention.

Turning now to FIG. 8, the method 62 of fabricating an antimicrobial agent delivery system is shown. Specifically, step 64 provides for coupling a hub to an antimicrobial agent-bearing rod. Step 66 provides for extruding a delivery tube. Step 68 provides for forming a longitudinal partition and a hub opening in the delivery tube. Step 70 provides for disposing the rod within the delivery tube, where the hub opening provides external access to the hub. It should be noted that method 62 may further include the process of coupling an external arm to the hub, in which case the step of disposing the rod within the delivery tube would include having the extension arm extend through the hub opening. Alternatively, the rod may have a flex point, where the hub is disposed outside the delivery tube. It should also be noted that a wide variety of cutting systems, such as a laser cutting system or a mechanical cutting system, can be used to form the longitudinal partition and the hub opening at step 68. Also, step 64 may come after steps 66 or 68.

While the invention has been described with reference to what are presently considered to be preferred embodiments thereof, it is to be understood that the invention is not limited to the disclosed embodiments or constructions. On the contrary, the protection sought for the invention as defined in the appended claims is intended to cover various modifications and equivalent arrangements. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. An antimicrobial agent delivery system comprising:
an antimicrobial agent-bearing intervention device;
a hub coupled to the intervention device; and
a delivery tube comprising first and second ends for containing the intervention device, wherein the delivery tube facilitates handling of the intervention device and wherein said delivery tube comprises a longitudinal partition and, optionally, a hub opening adjacent the longitudinal partition;
wherein the hub extends at least partially outside the delivery tube through said longitudinal partition or said optional hub opening and wherein longitudinal movement of the hub ejects the intervention device from the delivery tube.

2. The delivery system of claim 1, wherein the longitudinal partition is a continuous slit.

3. The delivery system of claim 2, wherein the continuous slit is self-sealing.

4. The delivery system of claim 3, wherein the delivery tube comprises a low durometer thermoplastic polyurethane or polyethylene.

5. The delivery system of claim 1, wherein the delivery tube has a multiple lumen geometry defined by a first tube and a second tube, the intervention device being disposed within the first tube.

6. The delivery system of claim 1, wherein an outer surface of the delivery tube includes at least one of a polyether block amide (PEBA), thermoplastic polyurethane (TPU), polyester elastomer, ionomer and thermoplastic vulcanizate to provide a relatively high surface texture.

7. The delivery system of claim 1, wherein the antimicrobial agent includes iodine, and wherein the delivery tube has an inner surface that is non-permeable to iodine.

8. The delivery system of claim 7, wherein the inner surface of the delivery tube is polyester or a similar material non-permeable to the particular antimicrobial agent.

9. The delivery system of claim 1, further including a valve coupled to an open end of the delivery tube.

10. The antimicrobial agent delivery system of claim 1, wherein the longitudinal partition extends to the first end of the delivery tube.

11. The antimicrobial agent delivery system of claim 1, wherein said delivery tube comprises said hub opening.

12. A method of fabricating an antimicrobial agent delivery system comprising:
coupling a hub to an antimicrobial agent-bearing intervention device;
forming a longitudinal partition and, optionally, a hub opening in a delivery tube; and
disposing the intervention device within the delivery tube such that the hub extends at least partially outside the delivery tube through the longitudinal partition or the optional hub opening, wherein longitudinal movement of the hub ejects the intervention device from the delivery tube.

13. The method of claim 12, wherein the longitudinal partition is a continuous slit.

14. The method of claim 13, wherein the continuous slit is self-sealing.

15. The method of claim 12, wherein the delivery tube comprises a low durometer thermoplastic polyurethane or polyethylene.

16. The method of claim 12, wherein the delivery tube has a multiple lumen geometry defined by a first tube and a second tube, the intervention device being disposed within the first tube.

17. The method of claim 12, wherein an outer surface of the delivery tube includes at least one of a polyether block amide (PEBA), thermoplastic polyurethane (TPU), polyester elastomer, ionomer and thermoplastic vulcanizate to provide a relatively high surface texture.

18. The method of claim 12, wherein the antimicrobial agent includes iodine, and wherein the delivery tube has an inner surface that is non-permeable to iodine.

19. The method of claim 12, wherein the inner surface of the delivery tube is polyester or a similar material non-permeable to the particular antimicrobial agent.

20. The method of claim 12, further including coupling a valve to an open end of the delivery tube.

* * * * *